United States Patent [19]
George et al.

[11] Patent Number: 5,830,201
[45] Date of Patent: Nov. 3, 1998

[54] FLUSHABLE DIAPER AND METHOD

[75] Inventors: Frederick W. George, 117 Memorial Ave., Christchurch, New Zealand; Virginia C. George, deceased, late of Christchurch, New Zealand, by Frederick W. George, executor

[73] Assignee: Frederick W. George, Christchurch, New Zealand

[21] Appl. No.: 862,792

[22] Filed: May 23, 1997

Related U.S. Application Data

[63] Continuation-in-part of Ser. No. 795,232, Feb. 10, 1997, which is a continuation-in-part of Ser. No. 182,807, Jan. 14, 1994, abandoned.

[51] Int. Cl.$^6$ .................................................. A61F 13/15
[52] U.S. Cl. ...................................... 604/364; 604/385.1
[58] Field of Search .................................. 604/368, 358, 604/385.1, 364, 393, 394, 395, 387, 398–399

[56] References Cited

U.S. PATENT DOCUMENTS

| | | |
|---|---|---|
| 3,035,578 | 5/1962 | Elmore . |
| 3,370,590 | 2/1968 | Hokanson et al. . |
| 3,395,708 | 8/1968 | Hervey et al. . |
| 3,542,028 | 11/1970 | Beebe . |
| 3,658,064 | 4/1972 | Pociluyko . |
| 3,665,923 | 5/1972 | Champaigne, Jr. . |
| 3,670,731 | 6/1972 | Harmon . |
| 3,838,695 | 10/1974 | Comerford et al. . |
| 3,890,974 | 6/1975 | Kozak . |
| 3,901,236 | 8/1975 | Assarsson et al. . |
| 4,338,371 | 7/1982 | Dawn et al. . |
| 4,578,073 | 3/1986 | Dysart et al. ............................ 604/397 |
| 4,615,695 | 10/1986 | Cooper .................................... 604/385 |
| 4,685,916 | 8/1987 | Enloe ....................................... 604/385 |
| 4,798,603 | 1/1989 | Meyer et al. ............................ 604/378 |
| 4,964,857 | 10/1990 | Osborn .................................... 604/395 |
| 4,968,312 | 11/1990 | Khan ..................................... 604/388.1 |
| 5,026,363 | 6/1991 | Pratt ..................................... 604/385.1 |
| 5,037,410 | 8/1991 | Zimmerman et al. .................. 604/358 |
| 5,074,854 | 12/1991 | Davis ................................... 604/385.1 |
| 5,108,385 | 4/1992 | Snyder .................................... 604/397 |
| 5,185,009 | 2/1993 | Sitnam .................................... 604/364 |
| 5,190,533 | 3/1993 | Blackburn .............................. 604/367 |
| 5,207,664 | 4/1993 | Blanco .................................. 604/385.2 |
| 5,300,358 | 4/1994 | Evers ...................................... 428/286 |
| 5,360,422 | 11/1994 | Brownlee et al. .................. 604/385.2 |
| 5,405,342 | 4/1995 | Roessler et al. ........................ 604/364 |

FOREIGN PATENT DOCUMENTS

| | | |
|---|---|---|
| 520576 | 4/1940 | United Kingdom . |
| 1 406 615 | 9/1975 | United Kingdom . |

*Primary Examiner*—Mark O. Polutta
*Attorney, Agent, or Firm*—Flehr Hohbach Test Albritton & Herbert LLP

[57] ABSTRACT

A flushable diaper for use on the body of an infant or adult. An envelope has inner and outer walls which are secured together at their outer periphery to form an inner cavity. The outer wall is comprised of a hydrophobic outer layer together with a hydrophilic inner layer. The inner wall is comprised of a hydrophobic outer layer together with a hydrophilic inner layer. The inner and outer walls are separated by an interior cavity which contains one or more containers. The container is comprised of either a single layer or a laminated wall which forms a chamber that encloses a charge of water. The laminated wall is comprised a hydrophobic inner laminate and a hydrophilic outer laminate. When manually ruptured, the containers release water into the double walled envelope, which causes disintegration of the hydrophilic inner layers of the double walls, along with the hydrophobic outer layers. An absorbent member is carried on the inner wall of the envelope, and the absorbent member comprises a fluid pervious cover which encloses an inner body that is comprised of a material which is sufficiently hydrophilic to absorb urine and other fluids from the body while maintaining structural integrity of the inner body and to also absorb water in an effective amount to cause the inner body to disintegrate into small pieces.

26 Claims, 2 Drawing Sheets

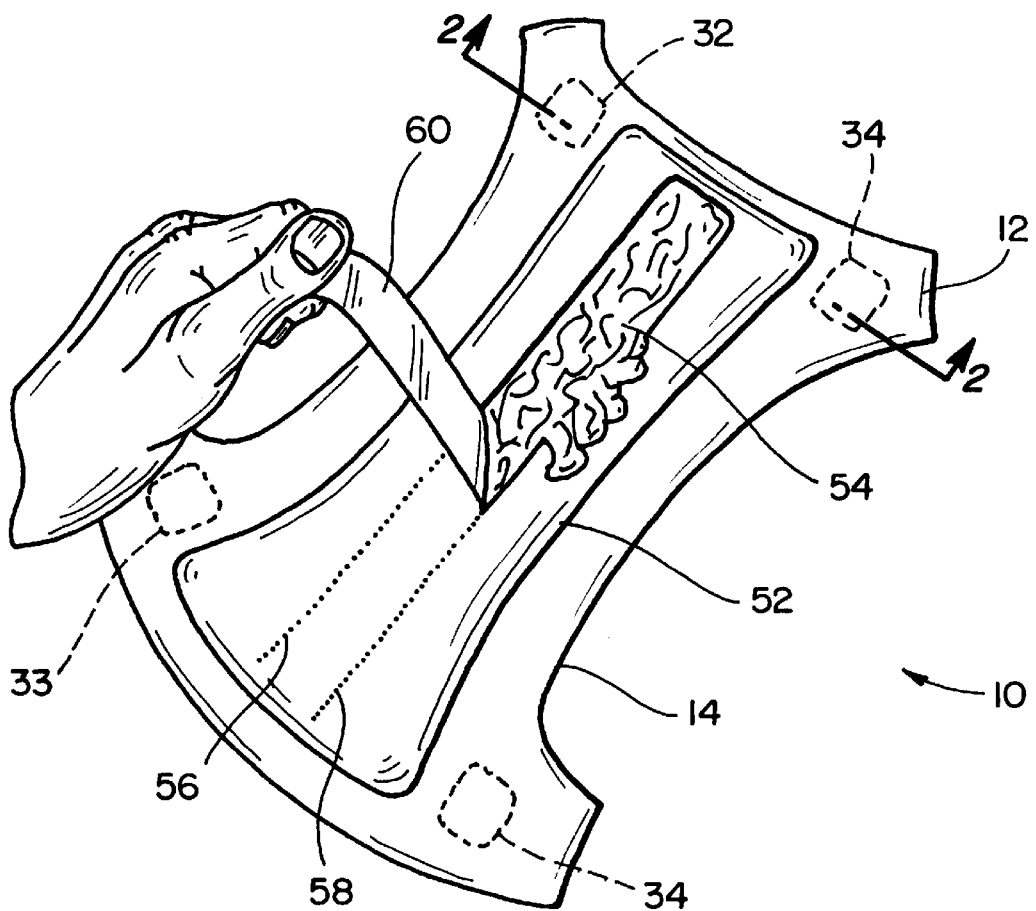
FIG_1
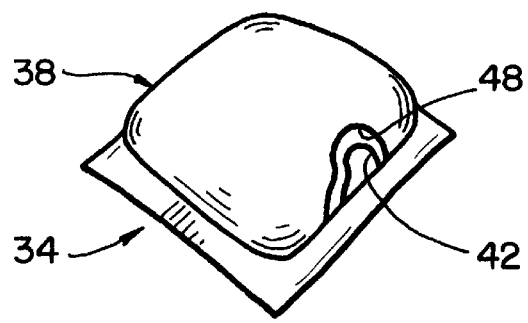
FIG_3

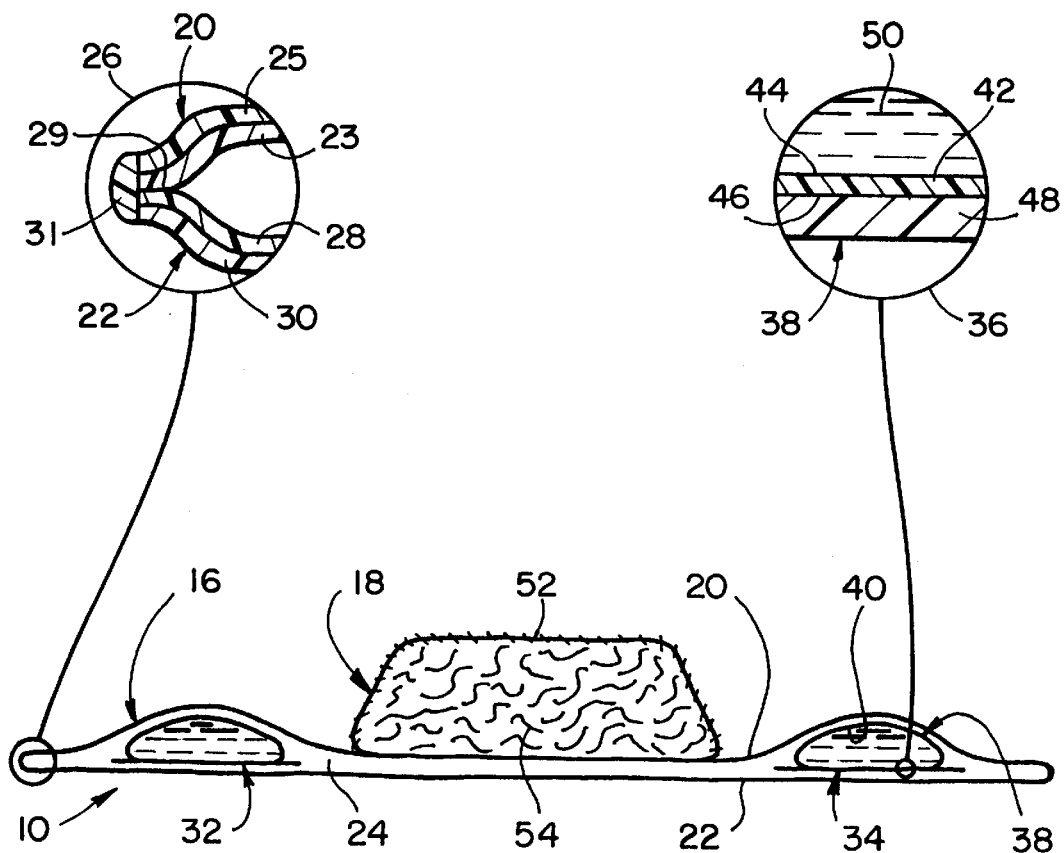
FIG_2
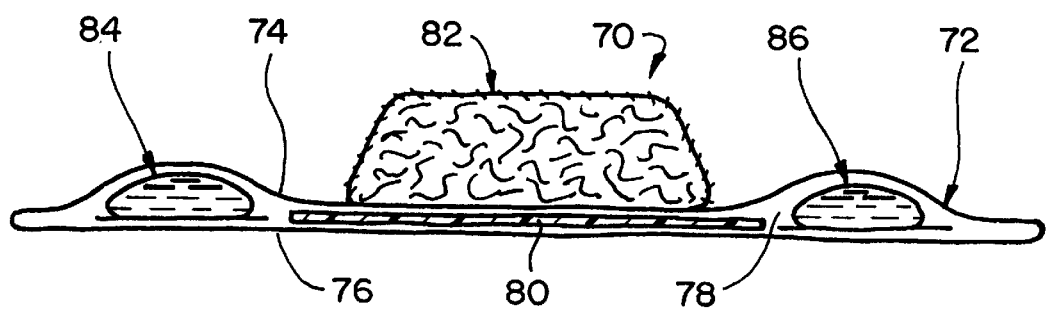
FIG_4

FLUSHABLE DIAPER AND METHOD

CROSS REFERENCE TO RELATED APPLICATIONS

This is a continuation-in-part of application Ser. No. 08/795,232 filed Feb. 10, 1997, which in turn is a continuation-in-part of application Ser. No. 08/182,807 filed Jan. 14, 1994 now abandoned.

BACKGROUND OF THE INVENTION

1. Field of the Invention

This invention relates in general to diapers for use with infants or incontinent adults. More particularly, the invention relates to a diaper in which the soiled components can be conveniently flushed in a toilet to obviate the problems of environmental contamination and health risks that commonly arise from disposable diapers.

2. Description of the Prior Art

Various diaper designs have been provided in the prior art in an effort to deal with the objectionable and burdensome problem of disposing of soiled diapers.

Among the prior art diapers is that disclosed in U.S. Pat. No. 4,964,857 to Osborn which provides a biodegradable outer part to absorb urine and a removable liner to flush feces away in a toilet while the outer part is disposed of in a landfill. Among the problems with this type of diaper is that urine acts a solvent for feces, carrying bacteria to the outer part, which then contaminates landfill. Landfill utilization is also a problem in view of the large number of diapers being disposed of by the general population. These same problems arise from the diaper disclosed in U.S. Pat. No. 4,578,773 to Dysart which also provides a disposable inner part and a reusable outer part.

Among the patents disclosing diapers having disposable components which are biodegradable are U.S. Pat. No. 5,037,410 to Zimmerman, U.S. Pat. No. 5,190,533 to Blackburn, U.S. Pat. No. 5,108,385 to Snyder, U.S. Pat. No. 5,207,664 to Blanco, U.S. Pat. No. 5,185,009 to Sitnam and U.S. Pat. No. 5,026,363 to Pratt.

U.S. Pat. Nos. 4,338,371 to Dawn and 4,798,603 to Meyer disclose disposable diapers which include gel materials for absorbing urine. U.S. Pat. No. 3,665,923 to Champaigne discloses a flushable sanitary napkin which disintegrates when exposed to an excess of water.

Many of the prior art diapers are disposed of in the user's garbage can or refuse container, which not only is inconvenient but can give rise to bad odors as well as significant occupational health risks to sanitary workers. In addition, the diapers are ultimately disposed of in landfills, which can lead to contamination of the soil or public water supply.

Conventional cloth diapers must be rinsed in a toilet bowl or other container to remove the bulk of feces, and then stored in diaper pails for home laundry or pick up by diaper services. This procedure gives rise to bad odors, burdensome laundering or the expense of the diaper service.

Many prior art diaper designs can also lead to discomfort of the infant, or even diaper rash, due to contact of the skin with diaper layers which absorb moisture and/or urine.

The need has been recognized for a flushable diaper which obviates the foregoing and other limitations and disadvantages of prior art diapers. Despite the various diapers in the prior art, there has not yet been provided a suitable and attractive solution to these problems.

OBJECTS AND SUMMARY OF THE INVENTION

The invention in summary provides a flushable diaper and method for wearing on the body of an infant or adult. The diaper comprises an envelope having inner and outer walls. The inner wall of the envelope is also comprised of a hydrophobic outer layer and a hydrophilic inner layer. The hydrophilic inner layers of the outer and inner walls absorb water in effective amounts to cause disintegration into small pieces. The inner and outer walls are sealed along their outer peripheries to form an interior cavity. At least one container within the interior cavity is comprised of either a synthetic plastic film or a laminated wall which contains a charge of water. The plastic film can be any of a variety of synthetics such as polyethylene, polypropylene or polyvinyl acetate. The laminated wall is comprised of a hydrophobic inner laminate and a hydrophilic outer laminate. The synthetic plastic film or the laminated wall is rupturable responsive to manually applied pressure for enabling the charge of water to egress from the container and discharge into the interior cavity. Attached centrally to the outer hydrophobic layer of the inner wall is an absorbent member. The absorbent member is comprised of an outer fluid pervious cover and an inner body. The inner body is formed of a material which is sufficiently hydrophilic to absorb urine and other fluids from the body and to also absorb water in an effective amount to cause the inner body to disintegrate into small pieces. A weakened tear path is formed in the cover for enabling a user to manually tear an opening through the cover to enable ingress of water sufficient to cause the absorbent material to disintegrate into small pieces.

The foregoing and additional objects and features of the invention will appear from the following specification in which the several embodiments have been set forth in detail in conjunction with the accompanying drawings.

BRIEF DESCRIPTION OF THE DRAWINGS

FIG. 1 is a perspective view of a flushable diaper in accordance with one embodiment of the invention.

FIG. 2 is a cross sectional view, to an enlarged scale, taken along the line 2—2 of FIG. 1.

FIG. 3 is a perspective view, to an enlarged scale, showing a component of the diaper of FIG. 1.

FIG. 4 is a cross sectional view similar to FIG. 2 showing another embodiment of the invention.

DESCRIPTION OF THE PREFERRED EMBODIMENTS

FIGS. 1 and 2 illustrate generally at 10 a flushable diaper in accordance with one preferred embodiment of the invention. Diaper 10 is of the wrap-around type with an hourglass shape. Suitable fastener tabs 12 are provided for fastening opposite ends of the diaper together. Cut-outs 14 are formed in the diaper for wrapping around the legs of the infant, or the legs of an invalid or incontinent adult, as the case may be.

Diaper 10 is comprised of an envelope 16 and an inner absorbent member 18 which is adhered by means such as adhesive to the envelope.

Envelope 16 is comprised of an inner wall 20 and outer wall 22. The outer wall faces in an outward direction from the body of the infant or adult, while the inner wall faces toward the body. The outer peripheries of the inner and outer walls are joined together and sealed to create an interior cavity 24. As shown in the enlargement of the peripheral edge at 26 (FIG. 2), the outer wall is comprised of an inner layer 28 and an outer layer or film 30 of a suitable waterproof material coated on the outer surface of the inner layer. In this embodiment, inner layer 28 of the outer wall is comprised of polyvinyl alcohol (PVOH) having a thickness in the range of 10 to 75 microns and film 30 is comprised of poly(vinylidene) dichloride (PVDC), which is a copolymer of polyvinyl chloride and vinylidene chloride. Also in this embodiment, inner layer 23 of the inner wall 20 is comprised of PVOH having a thickness in the range of 10 to 75 microns and outer layer 25 is comprised of PVDC. The PVDC film is sufficiently hydrophobic to be impervious to water and body fluids.

Also as shown in the enlargement at 26, the seal between the perimeter portions of the inner and outer walls is formed by a seam 29 which can be created by suitable means such as thermal bonding or ultrasonic welding, or by using small amounts of water to bond the interfacing surfaces of the PVOH material which form inner wall and the inner layer of the outer wall. Edges of the walls could be folded when the seal is formed, as desired. Any external exposed edges of the PVOH layers are sealed by a coating 30 which can be of either PVDC or wax.

One or more small water-filled waterproof containers 32, 34 are mounted in spaced-apart positions within interior cavity 24 of the envelope. In this embodiment four of the containers are positioned in the relationship shown in FIG. 1. These containers are of the type commonly known as "suicide bags" in biology, and are similar in concept to the lysosomes in biological living cells. Lysosomes are enzyme-filled inclusion sacs in a living cell which can be ruptured for various reasons to enable the cell to self-destruct. Container 34 is typical of the multiple containers and is formed by a laminated wall 38 which encloses a chamber 40. As best shown in the enlarged portion at 36, the laminated wall is comprised of an inner laminate 42 having an inner surface 44 and an outer surface 46, together with an outer laminate 48 which is carried on the outer surface of the inner laminate. The inner laminate is comprised of a hydrophobic material such as PVDC which holds a charge of water 50 within chamber 40. The containers are suitably sized to hold water charges in the range of 1 to 8 cc of water each. The outer laminate is comprised of a hydrophilic material such as PVOH or other synthetic polymers such as polyethylene, polypropylene or polyvinyl acetate. The material and thickness of outer laminate 48 are suitably selected so that the laminated wall has a structural strength which is sufficiently strong to normally contain water within the container when the diaper is being worn, and in which the structural strength is further sufficient to enable a predetermined amount of force applied against the laminated wall, such as by digital pressure from the user's hand, to rupture the container. This rupture occurs as the laminated wall is torn by the applied pressure to create an opening. The charge of water egresses from the chamber through the opening and discharges into interior cavity 24. Similarly, the container may be alternatively made of single layer, non-laminated, hydrophobic, synthetic plastic film such as polyethylene, polypropylene or polyvinyl acetate or the like. This container contains a charge of water and is to be ruptured with digital pressure similarly. Although this single layer container does not quickly disintegrate as the laminated container does, because of its small size and bulk it does not cause a stoppage problem in the toilet or plumbing.

Absorbent member 18 is comprised of a fluid pervious cover 52, formed in the shape of an elongate closed bag, which encloses an inner body 54. The fluid pervious cover is comprised of a suitable synthetic polymer material. Inner body 54 is comprised of a hydrophilic material which absorbs excretory fluid, such as urine, in an effective amount to maintain the layer's structural integrity and to also absorb water in an effective amount to form a colloidal suspension with the material of the inner body to break down the inner body's structural integrity.

The hydrophilic material of inner body 54 is comprised of a synthetic hydrogel polymer of the type which forms a colloidal suspension with water, together with a hydrophilic material. The synthetic hydrogel polymers disclosed in U.S. Pat. No. 4,798,603 can be used in the present invention except that the molecules of the polymers are sufficiently free of cross-linking so that they are water soluble. The synthetic hydrogel polymers suitable for use in inner body 54 include carboxymethyl cellulose, alkali metal salts of polyacrylic acids, polyacrylamides, polyvinyl alcohol, ethylene maleic anhydride copolymers, polyvinyl ethers, hydroxy propyl cellulose, polyvinyl morpholinone, polymers and copolymers of vinyl sulfonic acid, polyacrylates, polyacrylamides, polyvinyl pyridine, hydrolyzed acrylonitrile grafted starch, acrylic acid grafted starch, and isobutylene maleic anhydride copolymers and mixtures thereof.

The hydrophilic material of inner body 54 comprises inorganic high-absorbency materials which include absorbent clays and silica gel, and organic high-absorbency materials such as agar, pectin, guar gum, and peat moss. The inner body can be comprised of from 5% to 95% by weight of the hydrogel polymer and from 5% to 95% by weight of the hydrophilic material. Preferably the hydrogel polymer is distributed substantially uniformly throughout the mass of hydrophilic material.

Means is provided in pervious cover 52 to manually open up the absorbent member for infusing water into the inner body and to enable release of the colloidal suspension which is formed from the hydrogel polymer. In the illustrated embodiment this release means is comprised of small diameter perforations 56, 58 (FIG. 1) formed along a tear path across the cover 52. These perforations weaken the layer sufficiently so that a user can manually tear the envelope apart along the tear path to form a pull-away strip 60. The release means for the envelope could also be provided by a suitable weave in cover 52 by which the user can easily tear apart the cover. The release means could also be provided by a gum wrapper type tear string, or by a suitable adhesive layer which releasably fastens together preformed edges of the opening through which the water is to be infused.

Suitable attachment pads, not shown, formed on opposite sides at either end of the diaper can be provided to releasably hold the diaper about the lower torso of the infant or adult. The attachment pads can advantageously be comprised of pads of complementary hook and loop material (for example Velcro®) which releasably engage with material of the diaper itself, or alternatively with adhesive pads, not shown, sewn or otherwise secured to the opposite end of the diaper.

In use, the diaper is placed around and secured to the lower torso of the infant or adult by means of the attachment tabs so that absorbent member 18 is juxtaposed with the skin. Body fluids such as urine are wicked through pervious cover 52 of absorbent member 18 and into the hydrophilic material of inner body 54. The hydrophobic material of outer layer 25 of the inner wall of envelope 16 forms a waterproof barrier which prevents the body fluids from escaping the diaper and prevents wetting of the overlying clothes. The hydrophobic material of outer layer 30 of the outer wall of envelope 16 forms a waterproof barrier which prevents the body fluids from escaping the diaper and prevents the wetting overlying clothes.

The diaper is removed after it is soiled. Absorbent member 18 has absorbed and contained the feces and urine. The user then manually tears open cover 52 of the absorbent member by pulling strip 60 along the weakened tear path created by the perforations 56 and 58. Containers 32–34 are located by suitable markings, not shown, on the outside of the envelope and then manually and firmly pinched to rupture them. The charges of water within the container spread out through interior cavity 24 of the envelope. This facilitates dispersion of the water to all interior portions of the flattened envelope. The water dissolves the water soluble PVOH material of the inner layer 23 of the inner wall 20 and inner layer 28 of the outer wall. The PVOH material breaks down which in turn breaks down the PVDC waterproof coating 25 on the inner wall 20 and the PVDC waterproof coating 30 on the outer wall 22 of the envelope. The outer flattened envelope thereby "self destructs." The entire diaper, along with the manually opened absorbent member 18, is then dropped into the water within a toilet bowl. Water in the toilet then enters the opening in the absorbent member and infuses into inner body 54. The relatively large amount of water which is infused into the inner body forms a loose colloidal suspension with the hydrogel polymer sufficient to break down the inner body so that it loses its structural integrity. The colloidal suspension and hydrophilic material can then spill out the absorbent member opening and into the main part of the water in the toilet bowl. The entire diaper together with the colloidal suspension, the disintegrated pieces from the various layers and the feces and urine can then be easily flushed through the toilet without stopping it up. The materials which form the layers as well as the hydrophilic material and hydrogel polymer of the inner body, are treated as sewage and eventually biodegrade so that the water supply is not contaminated.

The diaper of the present invention is self contained to self-destruct. The diaper system of the present invention does not rely on any particular type of sewage disposal system for its breakdown. In certain countries, such as Austria, toilets do not have a water bowl, but instead have a slightly concave shelf with scant water on it. Toilets in New Zealand have only a small amount of water in the actual drain exit. In the American type of flush toilet, the diaper construction of the present invention speeds the ultimate breakdown of the diaper components in the water of the bowl by dissolving the components from the inside out. The components fragment into small pieces, which are finally dissolved in the water of the toilet with the flushing system.

The inner wall 20, and the outer wall 22, comprised of the PVDC coated layer of PVOH, will break down when the containers 32 and 34 are ruptured. These containers will also begin to break down the absorbent material of inner body 54 through the immediately adjacent inner wall 20 When cover 52 is manually opened as described above, water from the toilet bowl can immediately invade the material of inner body 54. This provides a secondary route of entry of water into absorbent member 18 to accelerate breakdown of the diaper.

FIG. 4 illustrates another embodiment providing a flushable diaper 70 comprised of an envelope 72 comprised of an inner wall 74 and outer wall 76. The inner and outer walls of the envelope are constructed in accordance with the corresponding inner and outer walls for the embodiment of FIGS. 1–3. Walls 74 and 76 are sealed at their peripheral edges, also in the manner explained in connection with the foregoing embodiment, to form an interior cavity 78. A planar sheet 80 of a suitable PVOH, cellulose, synthetic fabric or the like is carried within the internal cavity. An absorbent member 82, which is constructed in accordance with the corresponding absorbent member for the foregoing embodiment, is secured to wall 74. A plurality of water-filled containers 84 and 86 are positioned in spaced-apart relationship within cavity 78, and these containers are constructed in accordance with the corresponding containers described in connection with the foregoing embodiment.

When containers 84 and 86 are ruptured, water egressing from them wicks along hydrophilic sheet 80. This facilitates the spreading of water by the wicking action to increase breakdown of the hydrophilic components of the diaper.

While the foregoing embodiments are at present considered to be preferred it is understood that numerous variations and modifications may be made therein by those skilled in the art and it is intended to cover in the appended claims all such variations and modifications as fall within the true spirit and scope of the invention.

What is claimed is:

1. A flushable diaper for wearing on the lower torso of an infant or adult, the diaper comprising the combination of a sealed envelope having an inner wall and an outer wall forming a double wall construction, which cooperate to define an interior cavity, the outer wall facing in an outward direction away from the torso when the diaper is being worn and with the inner wall facing in an inward direction toward the torso, the outer wall being comprised of an inner layer and an outer layer, the outer layer being carried on a side of the inner layer which faces in the outward direction, the inner layer being comprised of a material which is sufficiently hydrophilic to absorb water in an effective amount to cause disintegration of the outer wall, the inner wall being comprised of an inner layer and an outer layer, the outer layer being carried on a side of the inner layer which faces in the inward direction, the inner layer being comprised of a material which is sufficiently hydrophilic to absorb water in an effective amount to cause disintegration of the inner wall, an absorbent member carried by the inner wall, the absorbent member having an inner body, the inner body being comprised of a material which is sufficiently hydrophilic to absorb urine and other fluids from the torso while maintaining structural integrity of the inner body and to also absorb water in an effective amount to cause the inner body to disintegrate, and a container within the interior cavity for containing a charge of water, the container having a structural strength which is sufficient to normally contain the charge of water when the diaper is being worn, and the structural strength further being sufficient to enable a predetermined amount of force applied against the container to cause the container to rupture and enable the charge of water to egress from the container and discharge into the interior cavity whereby the inner layer of the outer wall together with inner layer of the inner wall and the inner body of the absorbent member absorb respective portions of the charge of water which are sufficient to cause disintegration of the diaper.

2. A flushable diaper as in claim 1 and further comprising a cover having a tear portion which is sufficiently weak for enabling a user to manually tear an opening through the cover to enable, when the outer wall is submerged in a body of water, ingress of a portion of the body of water through the opening and into the absorbent member in an amount of water which is sufficient to cause the inner body of the absorbent member to disintegrate.

3. A flushable diaper as in claim 1 which the cover is comprised of a pervious material.

4. A flushable diaper as in claim 3 which the material of the inner and outer walls of the sealed envelope are comprised of polyvinyl alcohol.

5. A flushable diaper as in claim 1 which further comprises a sheet carried within the interior cavity, the sheet being formed of a material which is sufficiently hydrophilic to wick water along the internal cavity.

6. A flushable diaper as in claim 1 in which the outer layer is comprised of a hydrophobic material.

7. A flushable diaper as in claim 6 which the hydrophobic material is comprised of poly(vinylidene) dichloride.

8. A flushable diaper as in claim 1 in which the material of the inner layer is comprised of polyvinyl alcohol.

9. A flushable diaper as in claim 1 which the material of the inner wall is comprised of polyvinyl alcohol.

10. A flushable diaper as in claim 1 in which the sealed envelope is comprised of a double wall construction having an inner wall and an outer wall, which cooperate to define an interior cavity, which with the entry of water from the exterior into this interior cavity, between the double walls, the disintegration of the diaper is enabled.

11. A flushable diaper as in claim 1 in which the material of the inner body of the absorbent member comprises a hydrophilic composition having the property of absorbing water in an effective amount to form a colloidal suspension and break down the structural integrity of the inner body.

12. A flushable diaper as in claim 11 which the hydrophilic composition of the inner body is comprised of a hydrogel polymer which forms the colloidal suspension with water.

13. A flushable diaper as in claim 12 which the hydrogel polymer is comprised of molecules which are sufficiently free of cross-linking for absorbing water in an effective amount to form said colloidal suspension.

14. A flushable diaper as in claim 12 which the hydrophilic composition is further comprised of biodegradable cellulosic fibers.

15. A flushable diaper as in claim 1 in which the absorbent member is adhered to the inner wall of the envelope.

16. A flushable diaper as in claim 1 in which the inner and outer walls have outer perimeter portions which are sealed together.

17. A flushable diaper as in claim 1 in which the container comprises an exterior wall which encloses the charge of water, the exterior wall comprising a material selected from the group consisting of polyethylene, polypropylene, polyvinyl acetate and polyvinyl alcohol.

18. A flushable diaper as in claim 17 in which the polyvinyl alcohol is in a layer having a hydrophobic coating on the inner surface, which is in contact with the charge of water.

19. A flushable diaper as in claim 18 in which the hydrophobic coating is comprised of poly(vinylidene) dichloride.

20. A flushable diaper as in claim 1 in which the container is comprised of a laminated wall which at least partially encloses a chamber in which the charge of water is contained, the laminated wall having an inner laminate and an outer laminate carried on the outer surface of the inner laminate, the inner laminate being comprised of a hydrophobic material.

21. A flushable diaper as in claim 20 in which the laminated wall has a strength which is sufficiently weak to enable the laminated wall to rupture responsive to application of the predetermined force.

22. A flushable diaper as in claim 20 which the outer laminate is comprised of polyvinyl alcohol.

23. A flushable diaper as in claim 20 in which the hydrophobic material of the inner laminate is poly(vinylidene) dichloride.

24. A flushable diaper as in claim 1 in which the absorbent member has a fluid pervious cover surrounding at least a portion of the inner body.

25. A method of using a flushable diaper providing a flushable diaper for use on the lower torso of an infant or adult, the method comprising the steps of providing an envelope having an inner and an outer wall with the outer wall being comprised of a hydrophobic outer layer and a hydrophilic inner layer, and the inner wall being comprised of a hydrophobic outer layer and a hydrophilic inner layer, providing an absorbent member on the side of the inner wall which faces the lower torso when the diaper is being worn, the absorbent member comprising a fluid pervious cover and a hydrophilic inner body, passing excretory fluids from the lower torso through the cover and into the inner body, absorbing the excretory fluids into the inner body while maintaining the structural integrity of the inner body, infusing water into the inner body in an amount sufficient to form a colloidal suspension with the material of the inner body for breaking down the structural integrity of the inner body, providing a water-filled container within an interior cavity between the inner and outer walls with the container being comprised of a laminated wall having a hydrophobic inner laminate and a hydrophilic outer laminate, applying a force to rupture the container, releasing water from within the container and causing the water to be absorbed by the hydrophilic inner layers and the absorbent member.

26. A method as in claim 25 in which the diaper is placed into a body of water after the container is ruptured.

* * * * *